(12) United States Patent
Lemaire et al.

(10) Patent No.: US 8,444,854 B2
(45) Date of Patent: May 21, 2013

(54) PROCESS FOR THE TREATMENT OF WASTES COMBINING A PHASE OF TREATMENT BY METHANIZATION AND A PHASE OF THERMOPHILIC AEROBIC TREATMENT

(75) Inventors: Pierre Lemaire, Vence (FR); Beatrice De Lippe, Paris (FR); Fritz Ranke, Sceaux (FR); Dominique Martin, Paris (FR)

(73) Assignee: Societe Civile DLMR, Sceaux (FR)

( * ) Notice: Subject to any disclaimer, the term of this patent is extended or adjusted under 35 U.S.C. 154(b) by 425 days.

(21) Appl. No.: 12/744,116

(22) PCT Filed: Nov. 27, 2008

(86) PCT No.: PCT/IB2008/003670
§ 371 (c)(1),
(2), (4) Date: May 21, 2010

(87) PCT Pub. No.: WO2009/068995
PCT Pub. Date: Jun. 4, 2009

(65) Prior Publication Data
US 2011/0056260 A1    Mar. 10, 2011

Related U.S. Application Data

(60) Provisional application No. 61/019,034, filed on Jan. 4, 2008.

(30) Foreign Application Priority Data

Nov. 28, 2007   (FR) .................................... 07 59375

(51) Int. Cl.
*C02F 3/30*    (2006.01)

(52) U.S. Cl.
USPC .......... 210/603; 210/605; 210/613; 210/630; 210/259

(58) Field of Classification Search
USPC ................. 210/603, 605, 612, 613, 630, 252, 210/259
See application file for complete search history.

(56) References Cited

U.S. PATENT DOCUMENTS 5,342,769 A    8/1994   Hunter et al.
5,529,692 A    6/1996   Kubler
(Continued)

FOREIGN PATENT DOCUMENTS

FR    2 849 019 A    6/2004
GB    487 837 A    7/2005
WO    2004/035491 A1    4/2004

OTHER PUBLICATIONS

Search Report for International Serial No. PCT/IB2008/003670 dated May 20, 2009.
(Continued)

*Primary Examiner* — Fred Prince
(74) *Attorney, Agent, or Firm* — McCormick, Paulding & Huber LLP

(57) ABSTRACT

The present invention relates to the treatment of organic liquid and solid waste, comprising a first stage of treatment of the liquid content fraction of the waste by methanization, a second stage of treatment in a thermophilic or mesophilic aerobic phase of the semi-solid content fraction of the waste and a third stage in which said treated liquid and solid content portions are mixed in order to form a substrate, which is further treated by mesophilic or thermophilic aerobic phase treatment, resulting into compost.

18 Claims, 1 Drawing Sheet

U.S. PATENT DOCUMENTS

| | | | |
|---|---|---|---|
| 5,540,839 A * | 7/1996 | Pirt | 210/612 |
| 5,810,903 A | 9/1998 | Branconnier et al. | |
| 7,563,374 B2 * | 7/2009 | McWhirter et al. | 210/620 |
| 8,123,944 B2 * | 2/2012 | Haase et al. | 210/605 |
| 2003/0121851 A1 | 7/2003 | Lee, Jr. | |
| 2005/0145566 A1 | 7/2005 | Haase et al. | |

OTHER PUBLICATIONS

French Search Report for Serial No. 0759375 dated Jul. 2, 2008.

* cited by examiner

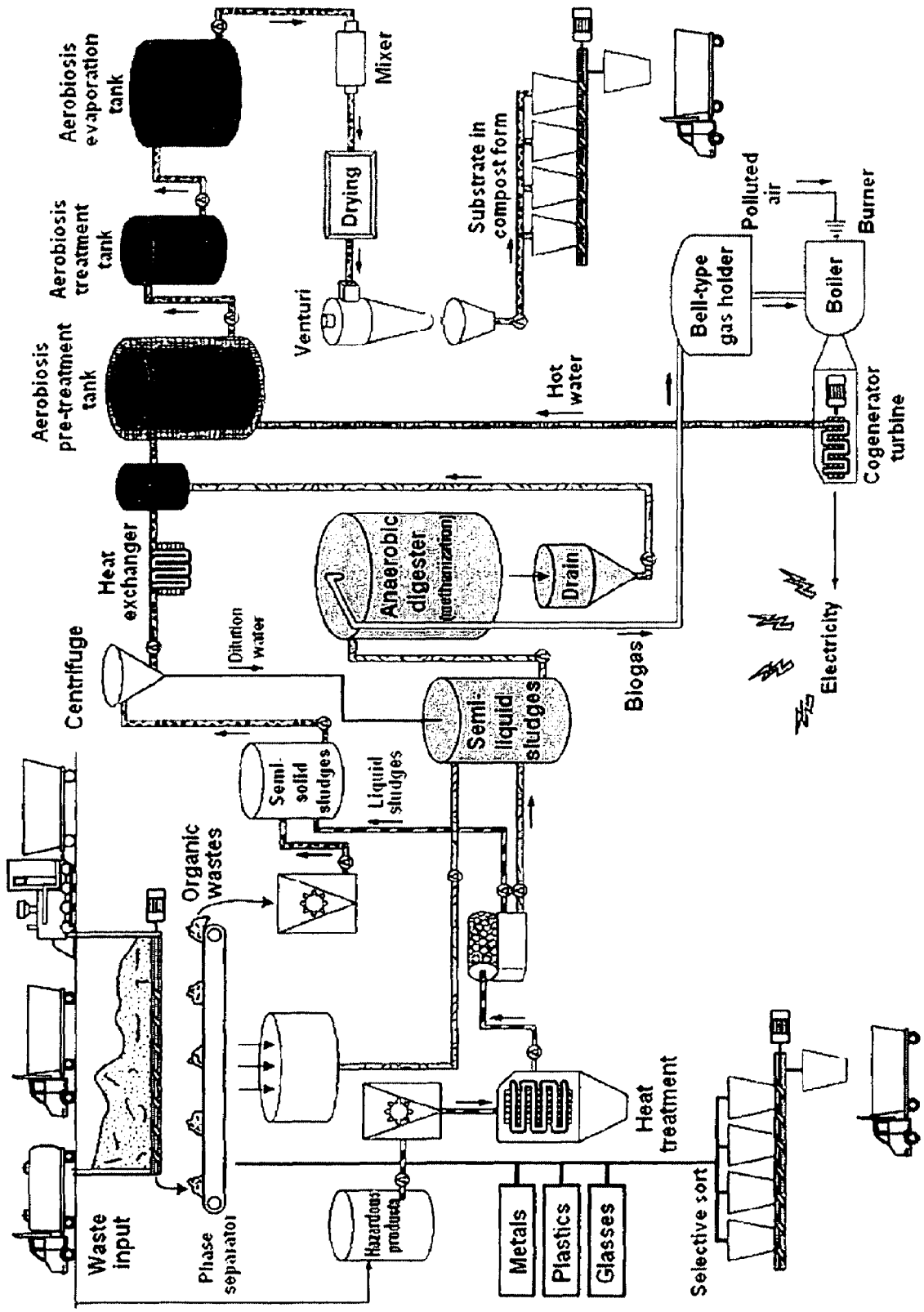

PROCESS FOR THE TREATMENT OF WASTES COMBINING A PHASE OF TREATMENT BY METHANIZATION AND A PHASE OF THERMOPHILIC AEROBIC TREATMENT

CROSS REFERENCE TO RELATED APPLICATIONS

This application is entitled to the benefit of and incorporates by reference essential subject matter disclosed in International Patent Application No. PCT/IB2008/003670 filed on Nov. 27, 2008; French Patent Application No. 0759375 filed Nov. 28, 2007; and U.S. Provisional Application Ser. No. 61/019,034 filed Jan. 4, 2008.

FIELD OF THE INVENTION

The present invention relates to the treatment of organic liquid and solid waste, comprising a first stage of treatment of the liquid content fraction of the waste by methanization, a second stage of treatment in a thermophilic or mesophilic aerobic phase of the semi-solid content fraction of the waste, and a third stage in which said treated liquid and solid content portions are mixed in order to form a substrate, which is further treated by mesophilic or thermophilic aerobic phase treatment, resulting into compost.

BACKGROUND OF THE INVENTION

With increasing population, disposal of organic waste has become a major cause for concern for public authorities. Indeed, it is well known that if organic wastes are not disposed of appropriately, simply sending them to landfill can lead to serious pollution of surface water and groundwater, and increase the risk of infectious agents.

The production of wastes increases in parallel with development in the standard of living. The consequences of this development are:
- an increase in the costs of waste treatment and disposal in order to protect the environment;
- an awareness of the limitation on raw materials and energy resources available to carry out the treatments.

Policies for sorting waste at source have been advocated, with the aim of removing a maximum amount of usable components from the waste in order to reduce problematic landfill tipping or undesirable incineration.

However, as regards the treatment of organic waste, sorting is difficult as both the sources and the type of waste are multiple: waste water, household waste, agri-foodstuffs industrial waste, green waste originating from the upkeep of open spaces, runoff water, etc.

Generally, organic wastes are collected separately, most frequently via the sewer system, and the problem arises mainly in terms of the volume and heterogeneity of the substrates requiring treatment.

A known method of "valorising" or extracting economic value out of organic wastes is their treatment by methanization, which involves treating the wastes by anaerobic fermentation in order to obtain biogas, i.e. a combustible mixture composed of methane and carbon dioxide.

Anaerobic fermentation is one of the natural processes which contribute to the breakdown of dead organic matter into simple gas and mineral elements. It is the result of a complex microbial activity which takes place essentially in two stages:

- hydrolysis, by which the macromolecules are decomposed into more simple products; this is a liquefaction or a gasification with conversion of the molecules to fatty acids, salts or also gases.
- conversion of its acids, salts or gases into methane and other gases.

The methanogenic bacteria, grouped under the *Methanobacterium, Methanobacillus, Methanococcus*, and *Methanosarcina* genera, form the principal part of the microorganisms involved in this type of fermentation.

They are characterized by a slow growth and live under strict anaerobiosis. Therefore, the conditions which are indispensable to methane synthesis in suitable fermenters called digesters are as follows:
- an anaerobic medium, as only decomposition in the absence of air leads to the formation of methane.
- a temperature allowing microbial activity between 10 and 65° C., as the enzymes of the methanogenic bacteria are destroyed beyond this temperature. Most frequently, methanization takes place at a temperature comprised between 20 and 40° C.

These conditions limit the volumes which can be treated, as in addition to containment, there is the time required for decomposition of the waste, which is approximately from a few days to several weeks, according to the volume and quality of the substrate.

Currently, two types of installation for continuous treatment of waste by methanization can be distinguished. The first type of installation is more particularly suitable for solid wastes and is found in technical landfill sites (TLS).

Technical landfill sites are sites of several hectares where wastes are appropriately stored. They are arranged in a favourable hydrogeological framework where it is possible to excavate cells of 10,000 to 1,000,000 m3 where the organic waste is disposed of and covered with earth. A venting device intended to recover the biogas is installed and the landfill gas is extracted by means of wells descending to 20 or 30 meters deep in the multiple layers of waste.

This type of installation requires substantial engineering investment, which is justified by the need to extract the underground gases from the landfill sites, which are greenhouse gases, presenting risks of explosion or soil contamination. These investments greatly exceed the proceeds of the sale of biogas to industry or even to consumers.

The second type of installation, which is more widespread, generally forms an integral part of large-scale conventional water treatment units (CWT) which treat the wastewater produced by hundreds of millions of inhabitants. Here treatments are carried out continuously. Firstly, pretreatment of the wastewater is carried out, allowing degreasing and the removal of matter in suspension, then the sludges obtained are treated by aerobiosis in order to activate the microorganisms contained therein. The wastes in the form of sludges are then introduced into a sealed digester equipped with a bell-type gas holder which makes it possible to trap the biogas under pressure while the organic matter is decomposed by the methanogenic microorganisms.

For reasons of productivity of this system, decomposition of the organic matter cannot be completed in the digester. The residues output from the digesters are therefore in the form of depleted sludges in which the load of organic matter remains too high for it to be discharged into rivers, spread on the fields, or dumped.

Thus on completion of the methanization treatment, these residues must be specifically treated or eliminated.

It will be shown that both types of installation for continuous treatment by methanization of organic wastes mentioned above, are present in large-scale installations, and for the time being do not constitute autonomous treatment units. Methanization units on a smaller scale do exist, for example for producing biogas from pig slurry, but these do not operate continuously.

Whatever the type of installation, it must be emphasized that the biogas produced by methanization is saturated with water and that it comprises other gases apart from methane, which are potentially dangerous. The biogas must therefore undergo treatment or enrichment steps to allow it to be sold, which currently makes its production uneconomic.

Moreover, an organic waste aerobic fermentation process is known, described in U.S. Pat. No. 5,810,903, using mesophilic or thermophilic microorganisms. This fermentation process operates at high temperatures comprised between 50 and 80 degrees, in the presence of an active oxygenation. The microorganisms which proliferate at this temperature allow a rapid breakdown of the organic matter and therefore an effective mineralization of the organic waste in short periods of the order of 24 to 48 hours.

The mesophilic and thermophilic microorganisms also have the advantage of being less sensitive to the pH variations which can arise during breakdown of the organic matter, which occurs in particular when the wastes have different origins.

These microorganisms generally preexist within the various substrates to be treated. Their growth is encouraged by the fact that the fermentation tanks are maintained at a high temperature, using an external heat source.

When these microorganisms are developed within the substrate formed by the wastes, the temperature inside the tanks is maintained in part by the microorganisms themselves, as most of them have an exothermic metabolism.

Under these high-temperature conditions, most of the active substances that can cause safety inconvenience in the recycling of organic wastes, such as medicines—including antibiotics—, synthetic hormones, pesticides, detergents and toxins, are mostly digested or destroyed. A sterilisation of the wastes can also take place during mineralization if the temperature is allowed to increase further. A final product is then obtained in the form of compost toxicologically and microbiologically safe. By compost, it is meant a solid product with dry matter content generally greater than 50% in weight, preferably greater than 70%, the composition of which is stabilized over a week or more.

This final product can be used in agriculture, for example as fertilizing compost in crop growing.

This thermophilic fermentation process is particularly advantageous in that it allows large volumes of organic waste to be converted rapidly, so that they can be converted into a useful organic and non-polluting product.

However, its implementation has certain drawbacks.

Firstly, it requires a considerable input of external energy, due to the need to bring a large volume of waste up to a temperature of around 50° C. This constraint requires heating installations which are not present in the conventional aerobic treatment systems operating at ambient temperature. In addition to the energy required for their operation, these installations impose an extra cost which is deemed excessive in relation to the productivity gain.

Secondly, activation of the fermentation requires an active supply of air having a sufficient oxygen content, which is generally pumped in at the base of the fermentation tanks. Finally, these are considerable volumes of air which have to come into contact with the microorganisms and which are then dispersed into atmospheric air. This air, which can be classified as contaminated, comprises malodorous effluvia which represent a genuine nuisance for residents living near this type of installation.

Thirdly, the wastes treated at the outlet of the tanks must preferably be dehydrated in order to be able to be transported under correct conditions, which, again, increase the energy consumption of this system.

It would therefore be necessary to improve the existing treatment devices using thermophilic microorganisms, in order in particular to make them more attractive in terms of costs and location.

Ideally, the public authorities would like to have available more compact waste treatment units which could be located underground, even in the basements of buildings and which being more numerous, could be better distributed over the country than large-scale units such as those we know today.

SUMMARY OF THE INVENTION

The purpose of the device according to the invention is to fulfil a certain number of these requirements, while mitigating or eliminating the drawbacks mentioned above.

According to the invention, a waste treatment unit using methanization by anaerobiosis may be coupled with a thermophilic or mesophilic treatment unit.

By means of this coupling, the volume dimensions of the methanization treatment unit are designed so that a sufficient quantity of energy in the form of biogas is supplied for the requirement of heating the walls of the treatment tanks in the mesophilic or thermophilic aerobiosis phase.

According to a particular embodiment, the polluted air which has provided the oxygenation of the anaerobiosis phase treatment is used to supply oxygen to the biogas combustion device. In this way, the process according to the invention makes it possible to avoid generating residues and odours requiring costly reprocessing and necessitating transport to external treatment units.

Thus, a treatment unit for carrying out the process according to the invention may be self-sufficient in energy, efficient in relation to the volume of waste to be treated, and compact due to the proximity of the different resources used within the same device.

These and other objects and advantages of the invention will be apparent from the description of embodiments of the invention which follow given by way of example in conjunction with the accompanying drawings.

BRIEF DESCRIPTION OF THE DRAWINGS

FIG. 1 gives a diagrammatic illustration of the self-sufficient modular treatment unit whose method of operation is described in the example. The arrows show the various flows of materials which can occur between the different resources used for treating the wastes. These flows are designed to reduce as far as possible the residues which must be treated outside the device. This unit corresponds to a developed form of the device according to the invention intended for self-sufficiency of the system as regards energy, and the generation of a final product in the form of compost.

DETAILED DESCRIPTION OF THE PREFERRED EMBODIMENTS

Thus, according to an aspect of the present invention there is provided a process for the treatment of organic wastes characterized in that it comprises a first stage of treating waste by methanization and a second stage of treating waste in a mesophilic or thermophilic aerobic phase.

In this process, the methanization treatment stage makes it possible to produce biogas, the energy from which is used to produce the heating necessary for treatment of the wastes in a mesophilic or thermophilic aerobic phase.

By the term "mesophilic or thermophilic aerobic phase treatment" is meant a process of biological treatment of organic wastes operated by mesophilic or thermophilic microorganisms in an enclosure where the oxygen level is close to that found in atmospheric air, i.e. between about 15% and about 25%. The mesophilic microorganisms develop at a temperature comprised between about 20° and about 50° C., and the thermophilic microorganisms between about 50° and about 80° C. Preferably, these microorganisms are present in the organic waste before being treated and are promoted by the temperature increase within the different substrates treated, but they can also be added in the form of concentrated spores or cultures during treatment, to activate the process.

By "substrate", it is meant a mixture of biotic and abiotic materials, which results from partial or total degradation of the organic waste by the microorganisms.

The treatment by methanization is performed according to the normal practice as regards fermentation by anaerobiosis of organic waste using methanogenic bacteria. The waste used can be the subject of a rigorous selection from the mixture of wastes to be treated, following the criteria known to a person skilled in the art, in order to obtain a more effective methanization. In this respect, the organic waste generated by the agri-foodstuffs industry, such as whey, distillery musts, abattoir effluent, which have a high carbon content, are preferred for implementation of this methanization stage. The process according to the invention encompasses as far as possible, treatment by methanization of a fraction only of the totality of waste undergoing the mesophilic or thermophilic aerobic phase treatment.

Generally, the treatment in the thermophilic aerobic phase comprises a first stage during which the different types of waste (liquids and solids) are homogenized in order to obtain a substrate in which the dry matter content is comprised between about 20 and about 50%, preferably between about 35 and about 45%. After an optional sorting stage assisted by mechanical handling equipment, the solid wastes are crushed and mixed with the necessary quantity of water. The water added may advantageously be wastewater and more advantageously be the residual water resulting from the methanization treatment stage.

In a second stage, the substrate is brought to a temperature which allows the development of the mesophilic or thermophilic microorganisms. Generally, heating the substrate is carried out in a first tank by convection, by heating the walls of the tank. In this respect, this first tank preferably has a hollow wall or a double wall, inside which the steam or hot water circulates. Preferably, the steam is heated by means of a boiler fuelled by the biogas obtained from the methanization treatment.

During a third stage, the substrate is sent to a second tank where the activity of the microorganisms is maintained by a permanent oxygen supply. This oxygen can be for example pumped from the base of the tank to the surface.

The metabolism of the microorganisms generally allows the temperature of the tank to be maintained between about 20° and about 100° C., preferably between about 40° C. and about 80° C., and more preferentially between about 50° C. and about 70° C. At this temperature, the majority of the chemical compounds, toxins, medicines or other active substances are destroyed.

A fourth stage makes it possible to convey the substrate into one or more tanks where it cools and through which the water is evaporated, so as to obtain a final substrate in a semi-solid form.

According to an aspect of the present invention, solid and liquid organic waste may be treated together in the same device and the following stages performed:
  milling the solid and liquid wastes;
  recovering a higher liquid content fraction of the waste, the dry matter content of said higher liquid fraction of the waste being between about 5 and about 20%, preferably between about 5 and about 10%;
  another fraction of the waste being a lower liquid content fraction having a dry matter content greater than 10%, preferably greater than 20%, is transferred to a thermophilic or mesophilic aerobiosis treatment unit;
  treating the higher liquid content fraction by methanization, to produce gas and using the gas to produce the heat required for treatment of the waste in the aerobic phase mesophilic or thermophilic treatment unit;
  then incorporating the methanized higher liquid content fraction with the lower liquid content fraction treated by thermophilic or mesophilic aerobiosis in order to obtain a substrate having a dry matter content comprised between about 10 and about 50%, preferably between about 20 and about 40%;
  treating the resulting substrate by mesophilic or thermophilic anaerobiosis; and
  recovering said treated substrate in the form of compost.

At the end of the mesophilic or thermophilic aerobiosis treatment phase, the process can comprise a final stage of drying or sterilizing the resulting treated substrate.

The substrate can for example be passed rapidly through an oven, which can also be supplied with energy by the biogas produced by methanization. The substrate is then inactivated and a compost is obtained which can be sold as organic fertilizer.

According to the invention, the residual water originating from the methanization is used to dilute the organic wastes treated during the mesophilic or thermophilic treatment phase.

Also, the residues originating from the first stage of treatment by methanization can be integrally incorporated into the wastes present in the thermophilic aerobic treatment phase.

The wastes treated by methanization then by thermophilic aerobiosis advantageously comprise a dried matter content comprised between 5 and 20%, preferably between 10 and 15%. Due to the fact that their nature is quite liquid, the residues of these wastes at the end of treatment by methanization can easily be incorporated into the substrate treated in the thermophilic aerobiosis phase.

The biogas produced during the stage of treatment by methanization is a mixture of gases constituted by at least 50% methane, the remainder being essentially $CO_2$ and water vapour. In the installations of the prior art intended to produce methane in large quantity, the fact that the biogas is not constituted by pure methane and that it is saturated with water, presents a obstacle to its valorization. Within the framework of the present invention, the biogas is intended to be burned on site, in particular to produce steam, it is therefore not a problem if the biogas is saturated with water and if it is impure. This steam is used to heat the tanks during the phase of treatment by mesophilic or thermophilic aerobiosis or to produce electricity. The electricity produced can, if necessary, also be used to heat said tanks via a heat exchanger.

According to a preferred aspect of the invention, the production of electricity makes it possible to provide for the energy demands of the device according to the invention for the implementation of the process according to the invention.

Thus according to the invention, the biogas energy is recovered by combustion of said gas. This combustion makes it possible to heat the walls of the tanks containing the wastes during the phase of mesophilic or thermophilic aerobic treatment by placing these walls in contact with hot water or steam, in order to promote the development of a flora of thermophilic or mesophilic microorganisms in the wastes.

According to a particular aspect of the invention, the air originating from the mesophilic or thermophilic treatment phase, which is loaded with effluvia due to diffusion through the treated substrate, is heat treated during combustion of the biogas originating from the first methanization treatment stage. In other words, the oxygen-loaded air which is pumped into the aerobiosis treatment tanks in order to activate the increase in the mesophilic or thermophilic microorganisms can be used according to the invention as a comburent for the biogas combustion. The combustion reaction makes it possible to destroy the compounds which form the foul-smelling effluvia contained in the air. It is thus possible to clean the air on exit from the device. This optional provision of the process makes it possible to reduce the olfactory pollution associated with the treatment in the mesophilic or thermophilic aerobic phase.

According to the invention, the stages of treatment by methanization and treatment in the thermophilic or mesophilic aerobic phase preferably take place in a continuous and/or simultaneous manner. The treatment is called continuous when it allows a regular supply of new waste to be treated. This does not necessarily imply a continuous input of waste into the treatment means that comprise the device. The treatment phases by methanization and aerobiosis are called simultaneous if they can be operated at the same time, independently of each other, in the same device.

A subject of the invention is also a device allowing the previously-described process to be implemented.

The invention relates in particular to a device for the treatment of organic wastes characterized in that it comprises at least one first means of treatment by methanization of the wastes and at least one second means of treatment of these same wastes by a mesophilic or thermophilic aerobic phase.

According to another aspect of the invention there is provided an installation for treating solid and liquid organic waste together there may be provided:
- an intake for waste in solid and liquid form;
- a milling apparatus for milling the waste;
- a separator for separating liquid and solid phases of the waste;
- a methanization unit for treating a higher liquid content phase of the waste;
- a mesophilic or thermophilic aerobic phase treatment unit for treating the lower liquid content phase of the waste under semi-solid state;
- a conduit or conveyor for transferring the methanized higher liquid content phase of the waste, to the mesophilic or thermophilic aerobic phase unit; and
- a homogenizing apparatus for homogenizing the higher liquid phase and semi solid lower liquid phase to form a semi-solid substrate subjected to mesophilic or thermophilic aerobic phase treatment.

As previously stated, an object of the present invention a compact treatment installation, which can treat various organic waste in both liquid and solid forms, preferably simultaneously. According to an embodiment, the mixing of liquid and solid organic waste, preferably after being milled and/or homogenised, are separated into two phases depending on their dry matter content. The higher liquid content phase is treated by methanization, and the lower liquid content phase, generally under semi-solid form, is treated in mesophilic or thermophilic aerobic phase. After treatment of the higher liquid content phase, said phase is mixed with the mesophilically or thermophilically aerobically treated lower liquid content phase, such as to form a substrate, the resulting substrate being further treated in mesophilic or thermophilic aerobic phase treatment. In an embodiment, the high liquid content phase is heated by combusting biogas produced by methanization, prior to forming the substrate. As indicated above, the means of treatment by methanization is generally a digester having average dimensions, as described in the prior art. The digester must be designed to collect the gas produced under anaerobiosis conditions.

According to a preferred aspect of the invention, the stage of treatment by methanization and the associated means are designed for the energy needs of the mesophilic or thermophilic treatment stage. Thus, the volume of the digester is preferably adjusted to produce a quantity of biogas in keeping with the energy required to implement the process according to the invention.

A treatment means in mesophilic or thermophilic aerobiosis phase according to the invention comprises at least one tank allowing microorganisms to be cultured under aerobiosis conditions in a substrate constituted by organic wastes. Preferably, said mesophilic or thermophilic aerobiosis treatment means is constituted by several fermenters linked together in series.

At least one of the tanks comprises a means of heat exchange allowing the organic wastes to be heated to the temperatures mentioned above. This heat exchange means can operate for example using an electrical resistance or by circulation of steam or hot water. Preferably, the substrate is heated by contact with the walls of the tank which are themselves in contact with said heat exchange means. The mesophilic or thermophilic aerobiosis treatment means advantageously comprise means of aeration of the substrate, which can be in the form of stirrers, such as screws or the input of pumped air at the bottom of the tanks. This means can also comprise other elements making it possible to optimize the mechanical operation of the aerobiosis treatment tanks known to a person skilled in the art. An example of an aerobiosis treatment means according to the invention is more particularly described in U.S. Pat. No. 5,810,903.

The device according to the invention generally comprises a means making it possible to transfer the wastes resulting from the methanization treatment to the means for treating said wastes by mesophilic or thermophilic aerobiosis. This means can for example take the form of a pipe connecting the digester directly to one of the aerobic treatment tanks, making it possible to drain the digester and to mix the methanization residues with the substrate treated by mesophilic or thermophilic aerobiosis.

According to a preferred aspect of the device, the means of treatment by methanization are combined with a boiler allowing the biogas produced by methanization to be burned, said boiler preferably being a co-generator making it possible to produce energy in the form of steam and/or electricity. This energy is then transferred from said boiler to said means of heating or preheating the wastes by means of energy transfer. In the case of electricity production, this means of transfer can take the form of electric cables connecting the generator which produces the electricity to the heat exchanger with which the aerobic treatment tank is equipped, and in the case of steam production, it can consist of a pressurized steam network connecting the steam power plant to said means of heating or preheating the wastes.

Depending on the type of wastes treated, it can be useful for the device to comprise upstream different means of sorting wastes according to their nature, and in particular a liquid/solid phase separator making it possible to adjust the water content of the wastes entering the different treatment means.

The following example is intended to complement the description without implying any limitation thereto.

EXAMPLE

Device According to the Invention in the Form of a Self-Sufficient Modular Treatment Unit The treatment unit comprises an intake through which the untreated organic wastes in solid and liquid form are introduced into the enclosure of the self-sufficient treatment unit. Using a phase separator, the liquid wastes are separated from the more solid wastes. The solid wastes undergo manual sorting on a conveyor belt in order to remove those which cannot be crushed. Wastes of this kind, such as for example pieces of wood, are incinerated in the boiler where the biogas is burned. The other wastes are crushed then transferred on a conveyor belt to a first tank of the thermophilic or mesophilic aerobic phase treatment unit, where they are stored. This first tank has a capacity of approximately 110 m$^3$. The liquid wastes are recovered by gravity at the level of a collector which opens out into a digester. The digester is in the form of a cylindrical tank having a capacity of approximately 3000 m$^3$. The liquid wastes are mixed in this cylindrical tank for a few hours until a mixture is obtained by evaporation, having a solid matter content adjusted to approximately 10%. The device comprises two digesters which operate alternately so as to have an almost continuous production of biogas. The first digester is started when the bell-type gas holder intended to recover the biogas under pressure is placed in a sealed fashion on the methanization tank. During the fermentation, the second digester which has finished its digestion cycle, and from which the bell-type gas holder has been removed, is emptied of its content. The methanization residues have a solid matter content approximately of the order of 10%. Their drainage out of the digester is carried out in a fluid fashion by a drain located at a low point of the digester. The fluid residues are conveyed by gravity, using a pipe extending said drain into the first tank of the thermophilic aerobiosis treatment unit where the substrate of solid or semi-solid wastes is stored. This first tank is equipped with screws which by turning enable the substrate to be homogenised. Pressurized hot water can be injected if necessary to improve the homogenization. This hot water makes it possible to bring the substrate to a temperature that is higher than the ambient temperature and to dilute the substrate until reaching a solid matter content of the order of 40%.

The biogas produced by the microorganisms during fermentation of the liquid wastes in the digester accumulated under the bell-type gasometer equipped with a valve, is conveyed through a tube to a burner located in a boiler where hot water and pressurized steam are generated.

The burner is equipped with a permanent source of ignition such that as soon as the biogas reaches the boiler it is immediately burned. The water vapour under pressure makes it possible to generate electricity by means of a turbine. This turbine, coupled to an electric transformer, makes it possible to provide for the energy needs of the unit which are of the order of 12500 Kw/h/day. The hot water is sent under pressure to the inside of the double wall made of Inox® of the second tank of the aerobiosis treatment unit, in order to heat the substrate contained in the tank until reaching a temperature of the order of 60° C. for several hours. The substrate is then transferred to a covered tank, the walls of which are insulated by a polyurethane foam lining. The aerobiosis treatment continues in this tank at a temperature greater than 50° C. for approximately 48 hours. At this stage, the temperature is maintained largely by the mesophilic or thermophilic microorganisms which develop in the substrate and by an active oxygenation.

The substrate is oxygenated continuously by pumping air in at the base of the tank. As the tank is covered, the air which is present at the surface of the substrate is sucked into an in Inox® pipe. This pipe opens into the combustion chamber of the boiler. The air loaded with effluvia which is recovered at the surface of the substrate in the tank thus serves as a comburent for the biogas combustion and the aromas contained in the effluvia are destroyed by thermal shock. The boiler is equipped with a chimney through which the combustion fumes are evacuated. This chimney is equipped with a filter to avoid the emission of dusts into the atmosphere.

During the treatment, the substrate will lose a large part of its water by evaporation. This loss of water can be replaced as required by hot water which is injected under pressure into the tank.

The substrate is then transferred by a pipe into a tank in the open air which is larger and shallower that the previous tank, having a depth of approximately 70 cm. The substrate is spread out in contact with the atmospheric air. It cools while losing water by evaporation and settling until reaching a semi-solid state in which the water content varies between 30 and 50%. After 2 hours, the substrate is taken up and transferred on a conveyor belt which passes slowly through the biogas combustion chamber in the boiler. The speed of travel of the conveyor belt in the combustion chamber is relation to the temperature of said chamber and the water content of the substrate at the input. In this way, the substrate is dried and sterilized in a relatively uniform fashion. The substrate then takes the form of a compost which is loaded into the tipper body of a lorry located at the end of the conveyor belt, for use as horticultural fertilizer.

While the present invention has been illustrated and described with respect to a particular embodiment thereof, it should be appreciated by those of ordinary skill in the art that various modifications to this invention may be made without departing from the spirit and scope of the present.

What is claimed is:

1. A process for the treatment of a mixture of solid and liquid organic wastes, wherein it comprises the following stages:
   milling the solid and liquid wastes;
   recovering a higher liquid content fraction of the waste, the dry matter content of said higher liquid fraction of the waste being between about 5 and about 20%;
   another fraction of the waste being a lower liquid content fraction having a dry matter content greater than 20% is transferred to a thermophilic or mesophilic aerobiosis treatment unit;
   treating the higher liquid content fraction by methanization to produce gas and using the gas to produce the heat required for treatment of the waste in the aerobic phase mesophilic or thermophilic treatment unit;
   then incorporating the methanized higher liquid content fraction with the lower liquid content fraction treated by thermophilic or mesophilic aerobiosis in order to obtain a substrate having a dry matter content comprised between about 20 and about 50%;

treating the resulting substrate by mesophilic or thermophilic anaerobiosis; and recovering said treated substrate in the form of compost.

2. The process according to claim 1, wherein the residual water originating from the methanization is used to dilute the organic wastes treated during the mesophilic or thermophilic aerobic treatment phase.

3. The process according to claim 1, wherein the residues originating from the first stage of treatment by methanization are integrally incorporated with the wastes present in the mesophilic or thermophilic aerobic treatment phase.

4. The process according to claim 1, wherein the stage of treatment by methanization is designed to suit to the energy requirements of the mesophilic or thermophilic aerobiosis treatment stage.

5. The process according to claim 1, wherein the gas energy is recovered by combustion of said gas.

6. The process according to claim 5, wherein the polluted air originating from the second mesophilic or thermophilic aerobic treatment phase is heat treated during the combustion of the gas originating from the first stage of treatment by methanization.

7. The process according to claim 1, wherein the walls of the tanks containing the wastes are heated during the mesophilic or thermophilic aerobic treatment phase in order to promote the development of a flora of thermophilic or mesophilic microorganisms in the wastes.

8. The process according to claim 7, wherein the walls of said tanks are maintained at temperature by placing them in contact with hot water or steam heated from the combustion of the gas produced by methanization.

9. The process according to claim 1, wherein the temperature of the wastes during the aerobiosis treatment is comprised between 50 and 80° C.

10. The process according to claim 1, wherein the process comprises moreover a final stage of drying or sterilization of the final product obtained at the end of the mesophilic or thermophilic aerobic treatment phase.

11. The process according to claim 1, wherein the stage of drying or sterilization of the sludges uses a part of the energy produced during the stage of treatment by methanization.

12. The process according to claim 1, wherein the stages of by methanization and treatment in thermophilic or mesophilic aerobic phase take place continuously and/or simultaneously.

13. A device for the treatment of organic wastes wherein it comprises:
an intake for waste in solid and liquid form;
a milling apparatus for milling the waste;
a separator for separating liquid and solid phases of the waste;
a methanization unit for treating a higher liquid content phase of the waste;
a mesophilic or thermophilic aerobic phase treatment unit for treating the lower liquid content phase of the waste under semi-solid state;
a conduit or conveyor for transferring the methanized higher liquid content phase of the waste, to the mesophilic or thermophilic aerobic phase unit; and
a homogenizing apparatus for homogenizing the higher liquid phase and semi solid lower liquid phase to form a semi-solid substrate subjected to mesophilic or thermophilic aerobic phase treatment.

14. The device according to claim 13, wherein the methanization treatment means are combined with a boiler making it possible to burn the biogas produced by the methanization.

15. The device according to claim 14, wherein said boiler generates energy in the form of steam or electricity.

16. The device according to claim 13, wherein said means for the treatment of wastes by mesophilic or thermophilic aerobiosis have a means of heating or preheating the wastes.

17. The device according to claim 16, wherein it comprises moreover, means for the transfer of energy from said boiler to said means of heating or preheating the wastes.

18. The device according to claim 13, wherein said mesophilic or thermophilic aerobic treatment means is constituted by several fermenters connected together in series.

* * * * *